United States Patent
Smits et al.

(10) Patent No.: US 6,475,163 B1
(45) Date of Patent: Nov. 5, 2002

(54) HEARING EVALUATION DEVICE WITH PATIENT CONNECTION EVALUATION CAPABILITIES

(75) Inventors: Matthijs P. Smits, Woodside, CA (US); Vineet Bansal, Santa Clara, CA (US); Abraham J. Totah, San Carlos, CA (US); Bryan P. Flaherty, Half Moon Bay, CA (US); Alfred Christian Walton, Belmont, CA (US)

(73) Assignee: Natus Medical, Inc, San Carlos, CA (US)

( * ) Notice: Subject to any disclaimer, the term of this patent is extended or adjusted under 35 U.S.C. 154(b) by 0 days.

(21) Appl. No.: 09/479,559

(22) Filed: Jan. 7, 2000

(51) Int. Cl.[7] .................................................. A61B 5/00
(52) U.S. Cl. ...................................................... 600/559
(58) Field of Search ................................ 600/559, 300, 600/544, 546, 378; 73/585

(56) References Cited

U.S. PATENT DOCUMENTS

| | | | |
|---|---|---|---|
| 4,308,873 A | * | 1/1982 | Maynard .................... 600/544 |
| 5,230,344 A | * | 7/1993 | Ozdamar et al. ............ 600/559 |
| 5,368,041 A | | 11/1994 | Shambroom ................. 128/731 |
| 5,413,114 A | * | 5/1995 | Zurek et al. ................. 600/559 |
| 5,916,174 A | | 6/1999 | Dolphin ....................... 600/559 |
| 5,954,667 A | * | 9/1999 | Finkenzeller et al. ....... 600/544 |
| 5,999,856 A | * | 12/1999 | Kennedy ..................... 600/559 |

* cited by examiner

Primary Examiner—Kevin Shaver
Assistant Examiner—Brian Szmal
(74) Attorney, Agent, or Firm—Orrick, Herrington & Sutcliffe LLP

(57) ABSTRACT

An apparatus and method for evaluation of hearing loss is disclosed. The apparatus and method use evoked Auditory Brainstem Responses (ABR) to determine if the subject is able to hear iteratively administered click stimuli. The present invention evaluates the sufficiency of the patient connections, namely earphones and electrodes, to the evaluation device. More particularly, the present invention determines if the earphones are detached or deformed, if the electrodes have been reversed, or if the electrodes have become detached.

30 Claims, 4 Drawing Sheets

HEARING EVALUATION DEVICE WITH PATIENT CONNECTION EVALUATION CAPABILITIES

RELATED APPLICATIONS

This application is related to the co-pending and commonly assigned U.S. Patent Application entitled "Hearing Evaluation Device with Predictive Capabilities," attorney Docket No. 8668-2027, filed by Matthijs P. Smits and Christopher M. Coppin and the U.S. Patent Application entitled "Hearing Evaluation Device with Noise Detection and Evaluation Capability," attorney Docket No. 8668-2029, filed by Matthijs P. Smits and Bryan P. Flaherty, the disclosures of which are hereby incorporated herein by reference.

1. FIELD OF THE INVENTION

The present invention relates to devices and methods that use electroencephalographic responses to auditory stimuli to evaluate hearing loss. More particularly, the present invention relates to devices and methods that use a subject's evoked electroencephalographic response to an auditory stimulus to determine if a subject may have hearing loss, and that are capable of detecting problems with the connection between the subject and the hearing evaluation device.

2. BACKGROUND OF THE INVENTION

In the past, hearing impairment in babies and children was often not detected until after it was observed that the baby or child did not respond normally to sound. Unfortunately, it often took months or even years for the parent to observe the impairment, and by that time the child's language and learning abilities were negatively and often irreversibly impacted. Indeed, recent studies indicate that the vocabulary skills of hearing impaired children markedly increases if their hearing loss is detected early. The optimal time to evaluate hearing loss is thus immediately after birth, both because early detection allows for early treatment, and because parents often fail to bring their infants to later appointments. As a result, a number of states have implemented programs to evaluate newborns for hearing loss.

However, babies, especially newborns, cannot participate in traditional hearing tests, which require the subject to indicate if he or she hears the auditory stimulus. Thus, devices and methods have been developed to objectively determine hearing loss, without the voluntary participation of the subject. One such method involves analysis of the involuntary electroencephalographic (EEG) signals that are evoked from a subject in response to an auditory stimulus. It has been found that when a subject is able to perceive a sound having particular characteristics, a specific EEG waveform known as an Auditory Brainstem Response (ABR) is generated. This ABR response signal is typically small in magnitude in relation to general EEG activity. Therefore, statistical and signal processing techniques have been employed and developed to help detect, to a predefined level of statistical confidence, whether an ABR response has in fact been evoked. ABR testing is especially applicable to evaluation of infants, but can be applied to any subject.

The stimulus is applied through a transducer, which is connected to an earphone covering the subject's ear. The earphone has a cavity that fits closely about the ear, and has an additional transducer, such as a microphone, that can detect ambient noise.

The ABR that is evoked in response to the auditory stimulus may be measured by use of surface electrodes on the scalp or neck. As a practical matter, the electrodes will also detect noise signals from neural activity (besides the ABR), muscle activity, and non-physiological environmental noise.

Thus, the device of the present invention is connected to the subject in two different ways. First, the earphone covers the ear, and creates a carefully defined acoustic environment through which the click stimulus is applied. Second, the electrodes detect the EEG signal of the subject.

There is potential for problems with both types of connections. If the earphone is incorrectly attached or deformed, the acoustic environment may be compromised and the accuracy of the testing can suffer. If the electrodes are reversed (i.e., the positive electrode placed where the negative should be and vice-versa), then the test data will be inverted, and the device will fail subjects who should pass.

Moreover, certain conditions can cause excessive impedance between electrodes, including certain skin conditions (such as excessively dry skin), or the detachment of the electrodes from the subject. Additionally, the wires connecting the electrode to the hearing evaluation device may become loose or detached. Excessive impedance, whatever its cause, can skew the data, and compromise or destroy the accuracy of the evaluation.

The present invention represents a major advance in the art because it provides means for evaluating the adequacy of the "patient connection" problems outlined above. The present invention continuously and automatically evaluates the acoustic environment created by the earphone, and notifies the operator of any inappropriate acoustic impedance resulting from detached or deformed earphones. It detects reversal of electrodes, and adjusts the hearing test accordingly. It also conducts electrode impedance and electrode "lift-off" tests, and uses a new protocol under which an impedance test is automatically conducted if "lift-off" is detected. The information provided by the impedance and "lift-off" test can be used by the operator to re-secure the electrodes as necessary.

The present invention thus enables quicker and more trouble-free evaluation, because it detects patient connection problems before significant time has been wasted. The present invention also improves the accuracy of such evaluation.

3. DESCRIPTION OF THE PRIOR ART

The prior art does not continuously and automatically scan for inappropriate acoustic impedance caused by deformed or detached earphones, nor does it detect and account for electrode reversal. Moreover, the prior art does not provide for the improved electrode impedance and lift-off detection of the present invention.

4. OBJECTS AND SUMMARY OF THE INVENTION

The present invention provides a device and method for use in analyzing the EEG signal evoked in response to the auditory click stimulus, to determine if the subject suffers from hearing loss. Broadly, the invention is directed to devices and methods that are capable of evaluating and maintaining proper connections (through the electrodes and earphones) between the subject and the device.

In one embodiment of the invention, evoked EEG responses to auditory stimuli are collected, and organized into "sweeps," with each sweep containing the response signal for one auditory stimulus. The sweeps are organized into B blocks, with each block b containing a predetermined number of sweeps $N_b$.

The response signal for each sweep is digitized and converted into a series of binary numbers corresponding to whether the amplitude of the response signal is positive or negative at various points. in time. The digitized, binary waveform is compared to a benchmark ABR waveform to determine if the ABR is present. To make this determination, a polarity sum is calculated, which represents the sum of the polarities of the response signals within all blocks at each measured point in time. Statistical techniques are then used to determine if an ABR is present, relying upon the expected distribution of polarity sums in the absence of an ABR. A "Pass" is triggered if the observed polarity distribution, as represented in a specifically defined test statistic, indicates that the likelihood that no ABR is present is below a predetermined threshold. After a certain predetermined number of blocks have been completed, evaluation. will cease if a "Pass" has not yet been triggered. Evaluation may also stop if the hearing evaluation device determines that the subject is very unlikely to pass the test. If the evaluation ends without a determination that the subject has passed, the subject will be referred for further testing to determine if he or she in fact does suffer from hearing loss.

These evaluation procedures depend on the maintenance of accurate patient connections. If the electrodes are reversed, a subject with normal hearing may fail the test. If the earphone is improperly attached or deformed, then the proper acoustic environment will not be created, and the test data could be compromised. If there is too much impedance between the electrodes (potentially caused by oily skin, excessively dry skin, defective or worn electrodes, or detachment of the electrodes), then the device cannot collect meaningful data.

The present invention addresses these patient connection problems. Therefore, it is an object of the present invention to detect reversal of the electrodes. It is a further object of the present invention to detect if the improper placement of the earphones or their deformation prevents the formation of the proper acoustic environment. It is also an object of the present invention to conduct electrode impedance and lift-off detection, to continuously test for electrode lift-off, and to conduct an electrode impedance test during periods of frequent electrode lift-off.

5. BRIEF DESCRIPTION OF THE DRAWINGS

Further features, elements, and advantages of the present invention will become apparent to a person of ordinary skill in the art in view of the following detailed description of a preferred embodiment of the present invention, made with reference to the drawings annexed, in which like reference characters correspond to like elements, and in which.

6. DESCRIPTION OF THE PREFERRED EMBODIMENT a. Overview

The invention disclosed herein detects, processes and analyzes the EEG response of a subject to certain sound stimuli. A click sound stimulus is repetitively applied to the subject's ear through a transducer. The click stimuli may be applied to one ear at a time (monoaurally), or to both ears simultaneously (binaurally). In the past, when binaural click stimuli have been applied, they have been applied at different frequencies. In a preferred embodiment, monoaural stimuli are applied at 37 Hz.

The click stimuli are applied to the subject through a sound transducer. The transducer is connected to the subject through an earphone. Although many different types of earphones could be used, a preferred embodiment of the present invention uses the earphones of U.S. patent application Ser. No. 09/395,799, filed by Sheehan et al The earphones described in U.S. Pat. Nos. 5,826,582 (Sheehan et al.), 5,913,309 (Sheenan et al.) and 4,930,250 (Liverani), are also suitable for use with the present invention.

Generally, such earphones are D-shaped, and create a cavity within which the subject's ear may be inserted. If an earphone is deformed, or is improperly attached, excessive ambient noise may be transmitted to the subject's ear. Additionally, deformation or improper placement of the earphone can comprise the acoustic environment within which the click stimuli are applied.

The EEG response is detected from surface electrodes. As noted above, the electrodes' ability to conduct electrical current can be impeded by oily skin, excessively dry skin, defective or worn electrodes, detachment of the electrodes from the skin, or detachment of connective wires from the electrodes. Excessive electrode impedance can skew the data, or in extreme cases prevent the collection of any meaningful data.

Figure 3:
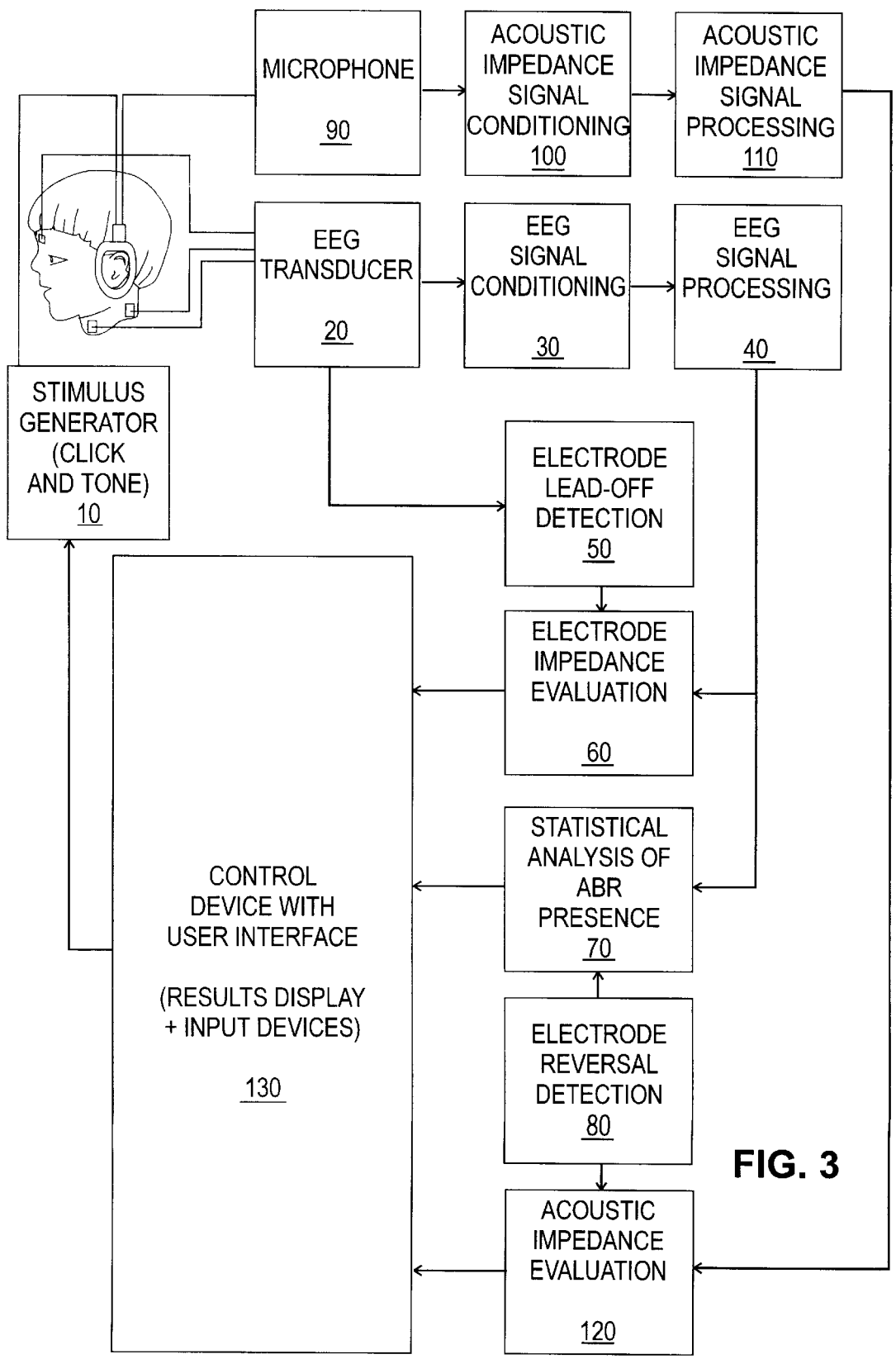
FIG. 3 is a block diagram of the components of the testing apparatus of the present invention.

In a preferred embodiment, the electrodes are placed on the subject in the following manner: a positive electrode is placed on the forehead, a negative electrode is placed on the nape, and a ground electrode is placed on the mastoid or shoulder (FIG. 3). Given the algorithms typically employed in hearing evaluation, a particular example of which is discussed below, it is often important that the electrodes not be reversed. If they are reversed, a hearing subject may fail the evaluation, and be needlessly referred for further testing.

The EEG signal detected from these electrodes is filtered so as to exclude signals that are not applicable to the ABR. The amplitude of the EEG response is digitized, and is assigned a binary value. This binary value represents the amplitude polarity of the waveform, that is, whether the EEG amplitude is positive or negative, at the measured time.

The stimuli and responses are grouped into "sweeps" and "blocks." A sweep is a response waveform to a single click stimulus. A block is a series of sweeps, and in a preferred embodiment, represents 500 accepted click stimulus responses. We refer to "accepted" click stimulus responses, because some sweeps may be rejected due to problems with the testing conditions.

Upon completion of a block of accepted sweeps, signal averaging is used to compute the composite waveform that results from this block. In addition, signal averaging is also used to compute the average composite waveform from all blocks combined. This average composite waveform is then compared with an internal template, to determine if the null hypothesis ($H_0$) can be rejected. The null hypothesis is the hypothesis that the baby is hearing-impaired, and will be rejected if the probability of an ABR being present is above a certain pre-set statistical threshold. In the preferred embodiment, the null hypothesis is rejected, and the evaluation ceases, when sufficient data has been collected to conclude, with 99.96% statistical confidence, that an ABR waveform is present. A "PASS" or other similar message may then be generated.

If the average composite waveform is insufficient to reject the null hypothesis, then the evaluation continues until the total number of sweeps exceeds a preset threshold, or until sufficient data have been collected to generate a "predicted refer," that is, a reference for further evaluation based upon a less-than-full-length evaluation.

b. Signal Analysis

The chief challenge in using ABR to evaluate hearing loss is the difficulty in determining the ABR response (if any) from the noise within which it is buried. This noise is typically Gaussian distributed, with a mean amplitude of zero, and with changing variance.

As stated above, the present invention detects the presence of an ABR by repetitively applying click stimuli in blocks b of $N_b$=500 sweeps. Each click stimulus is comprised of a 100 μs square pulse with, typically, a 35 dB nHL intensity level. The repetition rate for the clicks is 37 Hz. The polarities of the click stimuli are sequentially alternated between condensation (positive square pulse) and rarefaction (negative square pulse) stimuli. Since the noise has a mean of zero and no component is synchronous with the stimulus repetition rates, it is likely to sum toward zero with increasing sweeps, leaving the ABR.

Under the preferred embodiment of the present invention, the amplitude sequence of each click stimulus response is converted into a sequence of polarities (positive or negative) which, in turn, is summed with the other response polarity sequences in block b, to form the array $X_b$. For instance, an amplitude sample in the click stimulus response would be given a "1" if this amplitude were positive (no matter how high), and a "0" if this amplitude were negative (no matter how low). Thus, if no ABR were present, the expected proportion of polarities corresponding to the ABR template would be 0.5. However, if an ABR were present, the proportion would likely be higher. The proportion of polarities in an evoked response matching the ABR waveform is related to the amount of signal noise.

After each block of sweeps, the summed polarity sequence $X_b$ for block b is summed with the other summed polarity sequences into an array X. Also, the total number of sweeps N is calculated as the sum of the number of sweeps in each block:

$$\begin{cases} X = \sum_{b=1}^{B} X_b \\ N = \sum_{b=1}^{B} N_b \end{cases} \quad b = 1, 2, \dots, B$$

Figure 1:
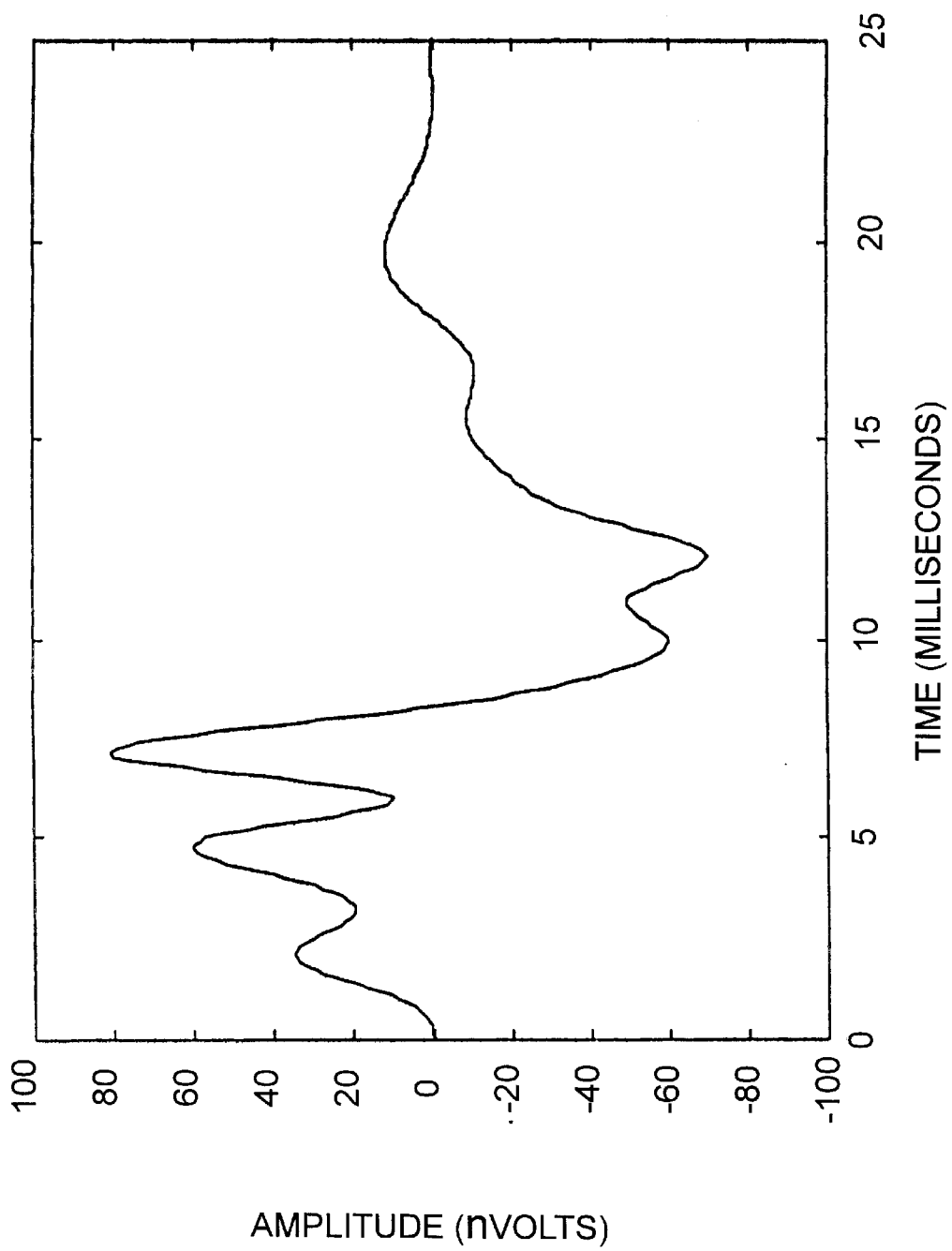
FIG. 1 illustrates a typical ABR waveform.
Figure 2:
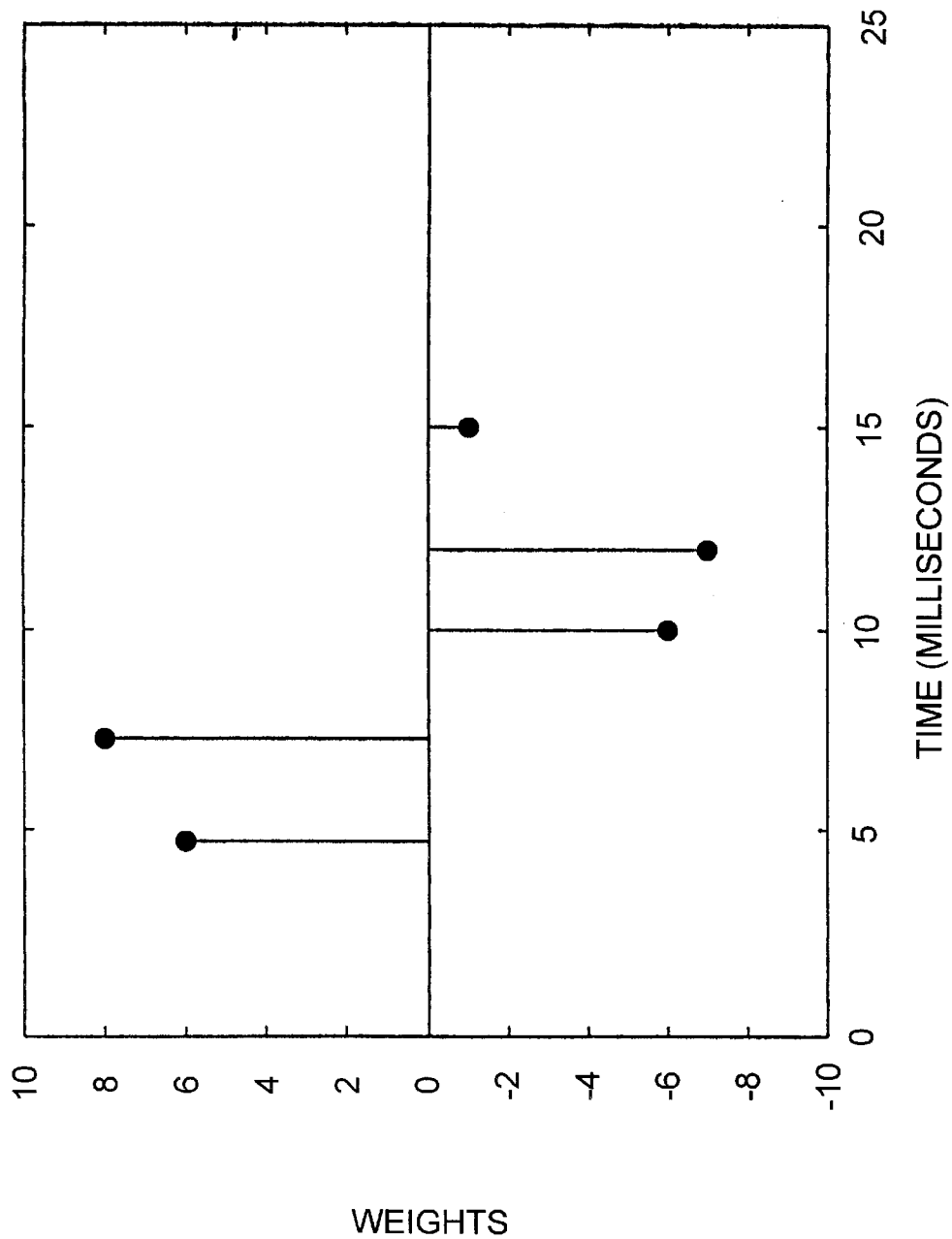
FIG. 2 illustrates a weighted ABR template.

The summed polarity sequence X is then compared with a template waveform, which has been compiled with the use of normative data (FIG. 1). This template is comprised of M weighted points, strategically placed to match the typical ABR waveform (FIG. 2). At each of the M points, a weight is assigned, reflecting the importance and polarity of the given measurement point in ascertaining the presence of an ABR, as derived from normative data. Thus, for any given point m, the sum of the polarities would be $x_m$. The sum of the weights equals zero.

The present invention uses a test statistic z to aid in determining if an ABR is present. This test statistic is defined as:

$$z = \frac{\sum_{m=1}^{M} w_m(x_m - \mu_x)}{\sqrt{Npq \sum_{m=1}^{M} w_m^2}}$$

where N is the number of sweeps, p is the probability of positive polarity, and q is the complementary probability. The test statistic z scores the random binary array X by multiplying its elements $x_m$ at each template point m with the corresponding weight $w_m$, and summing these results into a single, normalized number. In the absence of an ABR, the peak of the distribution of z would remain at zero, while in the presence of an ABR, the test statistic would grow with increasing number of sweeps N.

Subjects exhibit variability in the latency of the ABR waveform, so that different subjects, each of whom can hear, may exhibit ABR waveforms at different times after the click stimulus. In order to compensate for this variability, the test statistic z may be recalculated at various times. The highest z from each of these time-shifted samples, $z_{max}$, can be saved and used to determine the presence of the ABR. In a preferred embodiment of the present invention, a pass is indicated when $z_{max}$ reaches a value that is 4 standard deviations from zero.

The present invention also discloses a method and apparatus for detecting problems in the patient connections, i.e., problems with the earphones and electrodes. These aspects of the present invention are described below.

Figure 4A:
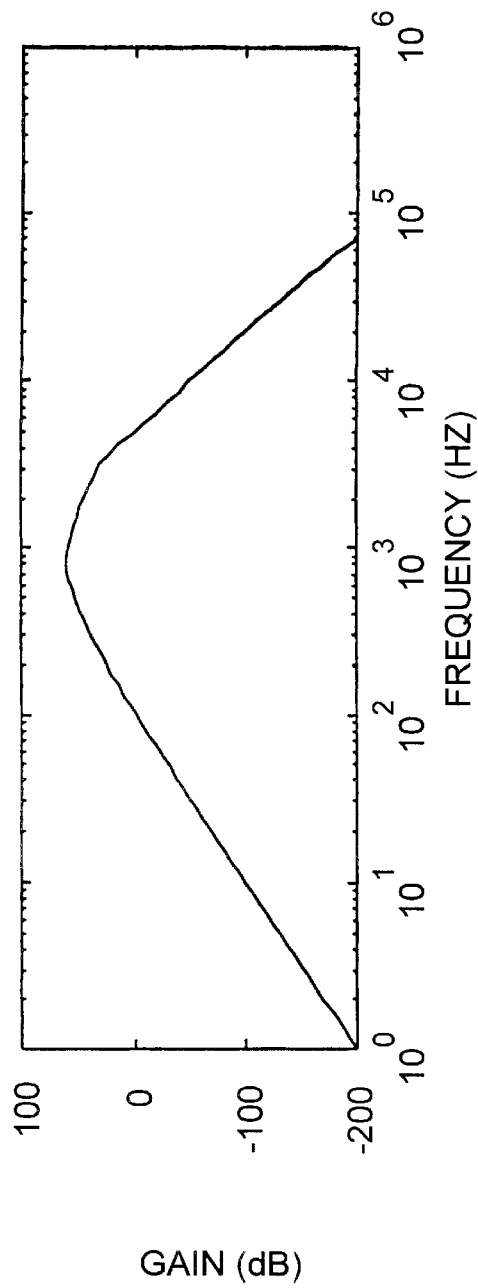
FIG. 4 is a bode plot for the acoustic impedance evaluation.
Figure 4B:
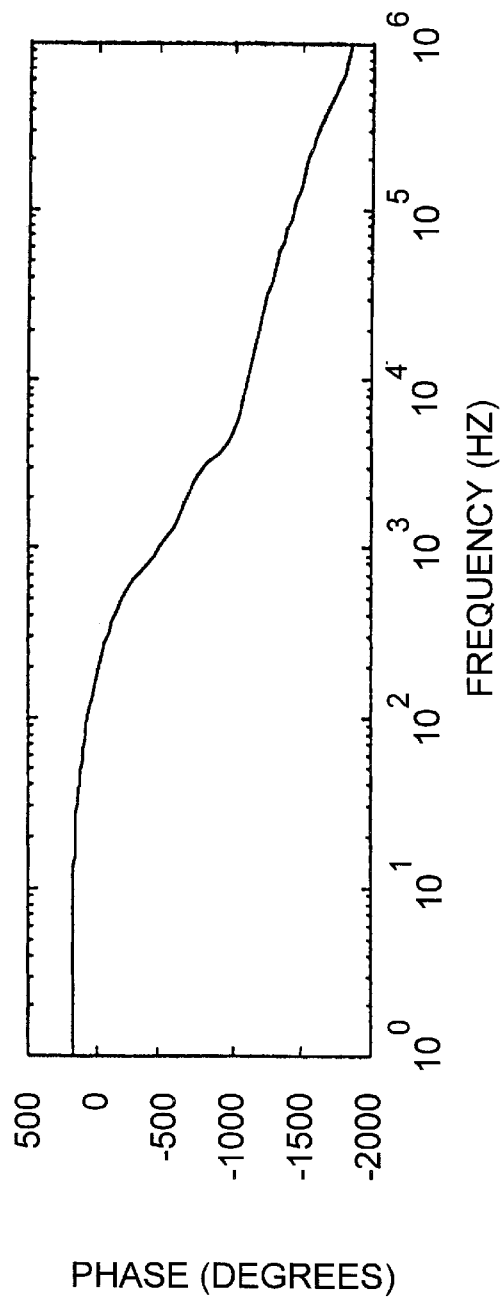

To detect inappropriate acoustic impedance, i.e., improper attachment and/or deformation of the earphones, an 800 Hz, 20 dB SPL tone is applied through the ear coupler. At approximately the same time, the microphone records the reflected signal, and hardware filtering is applied to create a bandpass filter around 800 Hz. (See FIG. 4).

The tone is a sine wave, and in a preferred embodiment, is applied to the earphone for a little more than a second. Starting 20 milliseconds from the onset of the tone, the microphone in the earphone collects 4,096 consecutive samples, one every 0.25 milliseconds. Using a power spectral density calculation with the Welch method, the response energy in the 800 Hz frequency range is then calculated, according to the following mathematical steps:

1. 31 sections of 256 consecutive samples are formed from the 4,096 samples, with each consecutive section starting at the mid-point of the previous section (50% overlap),
2. A Hanning window is applied to each 256-point sample section,
3. Each section is transformed with an 256-point FFT,
4. The periodogram of each section is formed by scaling the, magnitude squared of each transformed section,
5. The periodograms of the overlapping sections are averaged,
6. The average periodogram is scaled by the sampling frequency to form the power spectrum,
7. The level at the bin containing the 800 Hz frequency in the power spectrum is compared with pre-set thresholds.

If the amount of this energy is either below the pre-set lower-bound threshold, indicating "acoustic leakage" from an improperly placed earphone, or above the pre-set upper-bound threshold, indicating "excessive acoustic intensity" from a deformed earphone, then the acoustic impedance check has failed. The pre-set thresholds are derived through calibration with each device. In a preferred embodiment, this acoustic impedance check is conducted at the onset of the test and after the collection of each block of accepted sweeps, as well as upon determination that excessive ambient noise has been detected repeatedly.

The present invention may also be used with devices and methods to detect excessive ambient noise, as described in the co-pending and commonly assigned U.S. Patent Application entitled "Hearing Evaluation Device With Noise Detection and Evaluation Capability." In such a case, additional hardware filtering may be used with respect to the ambient noise signal, to create a bandpass filter around 800 Hz. Furthermore, in accordance with the present invention, acoustic impedance evaluation is conducted more frequently, if excessive ambient noise is detected at least 50% of the 100 sweeps since the last acoustic impedance check. Depending on the results of the acoustic impedance evaluations, the operator may re-apply the earphones to the subject.

The present invention also detects if the electrodes have been reversed. If electrodes are inverted, then $z_{max}$ decreases, rather than increases, with the number of sweeps. This would cause a hearing subject to fail, and therefore be needlessly referred for further testing.

To detect the possibility of such reversal, the inverted noise-weighted polarity sum, $\hat{X}^{inv}$ ($=-\hat{X}$), is applied to the same statistics z and $z_{max}$. This amounts to performing an evaluation test with the reversed polarities. Then, using both "regular" and inverted data, the present invention indicates electrode reversal if both of the conditions are met:

$$\begin{cases} z_{max} < 1 \\ z_{max}^{inv} > 4 \end{cases}$$

When electrode reversal has been detected, the present invention stops the evaluation and the user is asked to indicate whether the electrodes are reversed. If the user finds that the electrodes are indeed reversed and responds accordingly, the evaluation will be considered a "Pass." In the complementary case; the evaluation will produce a recommendation to repeat the test. Under such circumstances, the present invention cannot simply use the higher absolute $z_{max}$ value, because the template shifting described above makes the distribution of $z_{max}$ asymmetric.

The present invention also is directed to improved electrode impedance detection abilities. The prior art checked for electrode impedance, in the following manner. At the beginning of the test and after each block, an impedance test on each pair of electrodes is conducted. The test is conducted sequentially, in the following order: vertex-common (VC), nape-common (NC) and nape-vertex (NV). These tests are conducted by applying a 1 kHz, 10 µA peak-to-peak square wave to one of the electrodes, followed by a measurement at the other electrode that makes up the tested electrode pair. From this measurement, an impedance level is calculated, by means of the following principle:

$$Z = \frac{V_{in} - V_{out}}{I}$$

If the calculated impedance of one or more electrode pairs is greater than 12 kΩ, the most recent block is rejected.

In accordance with the present invention, electrode impedance evaluation is conducted more frequently, if electrode lift-off is detected at least 10% of the last 100 sweeps since the last electrode impedance check (see below). Depending on the results of the electrode impedance evaluations, the operator may re-secure the electrodes to the subject.

The present invention detects "lift-off" by applying a continuous 42 kHz, 10 µA square wave to the ground electrode, with continuous monitoring at both the nape and vertex electrodes. This monitoring is comprised of an electronic circuit, which applies a bandpass filter to both electrode signals around 42 kHz and determines the average amplitude levels at this frequency. In turn, these levels are compared against a pre-set threshold, representing the electrode "lift-off" condition. If either amplitude level exceeds this threshold, the circuit sets the binary output voltage to +5 V, indicating an occurrence of electrode "lift off." If electrode lift-off occurs frequently, namely 10% over a minimum of 100 sweeps since the last electrode impedance check, then evaluation pauses and an additional electrode impedance check is conducted, as described above.

The generation of the click stimulus and the acoustic impedance tone, the detection of the EEG response signal, the detection of the acoustic impedance tone, the processing and analysis of the EEG response signal, and the display of the results are performed by conventional electronic means, e.g. digital microprocessor controlled devices. Such devices include a transducer to generate the auditory stimuli, conventional electrodes to detect the EEG response signal, and a conventional microphone to detect the acoustic impedance tone. To analyze the EEG response signal a processing unit, such as a conventional microprocessor, and memory unit are needed. Additionally, a display unit and optionally an input device, such as a mouse and/or a keyboard, provide operator interface.

As shown in FIG. 3, stimulus generator 10 generates both the click and tone stimuli, and EEG transducer 20 detects the EEG response to the stimulus. Electrode lead off detection 50 occurs throughout the process, in accordance with the description provided above. When the EEG signal has been received, EEG signal conditioning 30 and signal processing 40 occur, readying the EEG response for analysis. Electrode impedance evaluation 60, statistical analysis for the presence of an ABR 70, and electrode reversal detection 80 then occur, as described above. Also during evaluation, microphone 90 detects the tone generated by stimulus generator 10, and acoustic impedance signal conditioning 100, acoustic impedance signal processing 110, and acoustic impedance evaluation 120 follow. Finally, a control device with user interface 130 displays the results.

One skilled in the art will appreciate that the present invention can be practiced by other than the preferred embodiments, which are presented for purposes of illustration and not of limitation. In addition, the specific parameter values identified herein are useful or representative parameter values, and it should be understood that other values or ranges of values for these parameters may be used without departing from the spirit and scope of the invention.

We claim:

1. A device for hearing evaluation of a subject comprising:
    means for repeatedly delivering auditory stimuli, said means creating a particular acoustic environment; and
    means for determining if said means for repeatedly delivering auditory stimuli is creating said particular acoustic environment.

2. The device according to claim 1, wherein said means for repeatedly delivering auditory stimuli comprises an earphone.

3. The device according to claim 1, wherein said means for determining if said means for repeatedly delivering auditory stimuli is creating said particular acoustic environment comprises:
  means for delivering an auditory tone, said auditory tone having an amplitude;
  means for detecting a response signal in response to said auditory tone;
  means for determining a response energy of said detected response signal; and
  means for determining if said response energy is outside a predetermined range.

4. The device according to claim 3, further comprising providing the predetermined range represents response energies indicating that the amplitude of said auditory tone has not significantly changed.

5. A system for hearing evaluation of a subject comprising:
  a transducer having an audible click output stimulus and a tone output stimulus, said tone output stimulus having an amplitude;
  an earphone, said transducer being located about said earphone;
  an electrode system adapted to detect an electroencephalographic (EEG) response to said click output stimulus;
  a microphone for detecting a response signal to said tone output stimulus; means for determining a response energy of said response signal; and
  processor for determining if said response energy is outside a predetermined range.

6. A system for hearing evaluation of a subject comprising:
  a first transducer having an audible click output stimulus;
  a second transducer having a tone output stimulus, said tone output stimulus having an amplitude;
  an earphone, said transducers being located in or about said earphone;
  an electrode system adapted to detect an EEG response to said click output stimulus;
  an microphone for detecting a response signal to said tone stimulus;
  means for determining a response energy of said response signal; and
  processor for determining if said response energy is outside a predetermined range.

7. The system according to claim 5 or 6, further comprising providing the predetermined range represents response energies indicating that the amplitude of said tone output stimulus has not significantly changed.

8. A method for hearing evaluation of a subject, comprising the steps of:
  repeatedly delivering auditory stimuli, through an earphone, said earphone creating a particular acoustic environment; and
  automatically determining if said earphone is creating said particular acoustic environment.

9. The method according to claim 8, wherein the step of automatically determining if said earphone is creating said particular acoustic environment comprises:
  applying a tone through said earphone apparatus, said tone having an amplitude;
  detecting a response signal to said tone stimulus;
  determining a response energy of said response signal; and
  determining if said response energy is outside a predetermined range.

10. The method according to claim 9, wherein the predetermined range represents response energies indicating that the amplitude of said tone has not significantly changed.

11. A device for hearing evaluation of a subject comprising:
  means for repeatedly delivering auditory stimuli;
  a pair of electrodes for sampling an EEG response to said stimuli, each electrode having a proper placement location; and
  means for determining if the placement location of said pair of electrodes is reversed relative to said proper placement location.

12. The device according to claim 11, further comprising:
  means for digitizing said EEG responses, said EEG responses having an amplitude polarity at each point of time;
  means for transforming said digitized EEG responses into a series of binary numbers corresponding to the polarity of the amplitude of said EEG response;
  means for transforming said binary numbers into an array of polarity sums;
  means for calculating a test statistic $z_{max}$ based upon said array of polarity sums; and
  means for determining the presence of an Auditory Brainstem Response (ABR) by analysis of the test statistic $z_{max}$.

13. The device according to claim 12, wherein said means for determining if the placement location of said pair of electrodes is reversed relative to said proper placement location comprises:
  means for calculating $z_{max}$ for the inverse EEG signal; and
  means for determining if the inverse of $z_{max}$ is above a first predetermined threshold,
  and if $z_{max}$ is below a second predetermined threshold.

14. The device according to claim 13, wherein the first predetermined threshold is 4, and the second predetermined threshold is 1.

15. A system for hearing evaluation of a subject comprising:
  a transducer having an audible click output stimulus;
  an electrode system adapted to detect an EEG response to said click output stimulus,
  said electrode system comprising a pair of electrodes, each electrode having a proper placement location; and
  a processor responsive to said electrode system for determining if the placement of said electrodes is reversed relative to said proper placement location.

16. A method for hearing evaluation of a subject, comprising the steps of:
  placing a pair of electrodes, each electrode having a proper placement location;
  repeatedly delivering auditory stimuli;
  sampling EEG responses to said stimuli with said pair of electrodes; and
  determining if the placement of said electrodes is reversed relative to said proper placement location.

17. The method according to claim 16, further comprising:
  digitizing said EEG responses, said EEG responses having an amplitude polarity at each point of time;
  transforming said digitized EEG responses into a series of binary numbers corresponding to the polarity of the amplitude of said EEG response;

transforming said binary numbers into an array of polarity sums;

calculating a test statistic $z_{max}$ based upon said array of polarity sums; and determining the presence of an ABR by analysis of the test statistic $z_{max}$.

18. The method according to claim 17, wherein the step of determining if the placement of said electrodes is reversed comprises:

calculating $z_{max}$ for the inverse EEG signal; and determining if the inverse of $z_{max}$ is above a first predetermined threshold, and if $z_{max}$ is below a second predetermined threshold.

19. The method according to claim 18, wherein the first predetermined threshold is 4, and wherein the second predetermined threshold is 1.

20. A device for hearing evaluation of a subject comprising:

means for repeatedly delivering auditory stimuli;

attachable means for sampling EEG responses to said stimuli; and means for continuously and automatically detecting if said sampling means are not attached.

21. The device according to claim 20, wherein the attachable means for sampling EEG responses to said stimuli comprises electrodes.

22. The device according to claim 21, wherein the means for continuously and automatically detecting if said sampling means are not attached comprises:

means for determining impedance between said electrodes; and means for determining if said impedance is greater than a predetermined threshold.

23. The device according to claim 22, further comprising providing the predetermined threshold as 12 kΩ.

24. A system for hearing evaluation of a subject comprising:

a transducer having an audible click output stimulus;

an attachable electrode system adapted to detect an EEG response to said click output stimulus;

an impedance detector for detecting the impedance associated with said electrode system; and a processor responsive to said detector impedance for continuously determining if said electrode system is attached.

25. A method for hearing evaluation of a subject, comprising the steps of:

attaching electrodes;

repeatedly delivering auditory stimuli;

sampling EEG responses to said stimuli with said electrodes; and continuously determining if said electrodes are attached.

26. A method for hearing evaluation of a subject, comprising the steps of:

attaching electrodes, said electrodes having an impedance between them;

repeatedly delivering auditory stimuli;

sampling EEG responses to said stimuli with said electrodes;

continuously determining if said electrodes are attached; and determining the impedance between said electrodes when it has been determined that said electrodes are not attached.

27. The method according to claim 26, wherein the step of determining the impedance between said electrodes when it has been determined that said electrodes are not attached comprises:

determining the percentage of time during which said electrodes are not attached; and determining the impedance between said electrodes when said percentage is below a predetermined threshold.

28. The method according to claim 27, wherein the predetermined threshold is 50%.

29. A device for hearing evaluation of a subject comprising:

means for repeatedly delivering auditory stimuli, said means creating a particular acoustic environment; and means for determining automatically if said means for repeatedly delivering auditory stimuli is creating said particular acoustic environment.

30. The device according to claim 29, wherein said means for repeatedly delivering auditory stimuli comprises an earphone.

* * * * *